United States Patent
Sakata et al.

[11] Patent Number: 5,958,776
[45] Date of Patent: Sep. 28, 1999

[54] METHOD FOR CLASSIFYING AND COUNTING IMMATURE LEUKOCYTES

[75] Inventors: Takashi Sakata, Kakogawa; Toshihiro Mizukami; Kayo Hatanaka, both of Kobe, all of Japan

[73] Assignee: Sysmex Corporation, Kobe, Japan

[21] Appl. No.: 08/972,103

[22] Filed: Nov. 17, 1997

[30] Foreign Application Priority Data

Nov. 20, 1996 [JP] Japan .................................. 8-309492
Oct. 22, 1997 [JP] Japan .................................. 9-289619

[51] Int. Cl.[6] .................................................. G01N 31/00
[52] U.S. Cl. ................................. 436/10; 436/8; 436/17; 436/63; 436/164; 436/166; 436/172; 435/29; 435/34; 435/39
[58] Field of Search .................. 436/8, 10, 17, 436/18, 63, 164, 166, 172, 800; 435/2, 29, 30, 34, 39; 252/408.1

[56] References Cited

U.S. PATENT DOCUMENTS

| | | | |
|---|---|---|---|
| 5,389,549 | 2/1995 | Hamaguchi et al. | 436/10 |
| 5,413,938 | 5/1995 | Tsujino et al. | 436/63 |
| 5,496,734 | 3/1996 | Sakata | 436/63 |
| 5,538,893 | 7/1996 | Sakata et al. | 436/10 |
| 5,618,733 | 4/1997 | Sakata et al. | 436/17 |
| 5,677,183 | 10/1997 | Takarada et al. | 436/10 |

FOREIGN PATENT DOCUMENTS

| | | |
|---|---|---|
| 0368652 | 5/1990 | European Pat. Off. . |
| 0424871 | 5/1991 | European Pat. Off. . |
| 0525397 | 2/1993 | European Pat. Off. . |
| 0525398 | 2/1993 | European Pat. Off. . |
| 0617281 | 9/1994 | European Pat. Off. . |
| 0678743 | 10/1995 | European Pat. Off. . |

OTHER PUBLICATIONS

H. M. Shapiro et al.,: "Combined Blood Cell Counting and Classification with Fluorochrome Stains and Flow Instrumentation". The Journal of Histochemistry and Cytochemistry, vol. 24, No. 1, Jan. 1976.

*Primary Examiner*—Maureen M. Wallenhorst
*Attorney, Agent, or Firm*—Pearne, Gordon, McCoy & Granger LLP

[57] ABSTRACT

A hematological sample is treated with a hemolytic agent that maintains immature leukocytes in a viable state and damages other leukocytes. The damaged leukocytes are stained with a fluorochrome which can stain damaged cells. At least one kind of scattered light and at least one kind of fluorescence of the treated and stained blood cells are measured to classify and count leukocytes based on the intensities of the scattered light and the fluorescence. Highly precise measurement of immature leukocytes and simultaneous classification and counting of normal leukocytes are achieved.

5 Claims, 4 Drawing Sheets

| INVENTION | MANUAL METHOD: 200 CELL COUNT |
|---|---|
| IG 3.5% | MYELOCYTES 2% |
| | METAMYELOCYTES 2% |

| INVENTION | MANUAL METHOD: 200 CELL COUNT |
|---|---|
| IG 7.5% | MYELOCYTES 3% |
| | METAMYELOCYTES 4% |
| BLAST 2% | MYELOBLASTS 2% |

METHOD FOR CLASSIFYING AND COUNTING IMMATURE LEUKOCYTES

BACKGROUND OF THE INVENTION

This invention relates to a method for classifying and counting leukocytes by flow cytometry.

In the field of laboratory examination, the classification and counting of leukocytes can give very useful information for diagnosis of disease. Usually, leukocytes in normal peripheral blood come in only five types, lymphocytes, monocytes, eosinophils, basophils and neutrophils. In various hematological disorders, however, immature leukocytes such as myelocytes and myeloblasts appear. Detection of these immature leukocytes is of utmost importance in diagnosing disease.

For this purpose, it has been a customary practice to prepare a blood smear, stain it appropriately, and observe the stained sample microscopically for classification and counting. In recent years, various fully-automated differential leukocyte counters utilizing the principle of a flow cytometer have been produced. These devices can perform highly precise classification and counting of normal leukocytes, but were unable to detect and classify the aforementioned immature leukocytes reliably.

Recent years have seen the provision of reagents and methods which detect the appearance of immature leukocytes highly precisely by the principle of RF/DC measurement (Japanese Laid-Open Patent Publication No. 273413/94).

The method of this publication measures immature leukocytes electrically by use of their nature that under specified conditions, they are less destructible than normal leukocytes. It has also been suggested that their measurement can be made based on information on scattered light. This method, however, aims only at the detection of immature leukocytes. Although it exhibits an excellent performance in the detection of immature leukocytes, the method cannot be used to classify and count normal leukocytes simultaneously with the measurement of immature leukocytes. Alternative methods need to be performed to classify and count normal leukocytes.

Japanese Laid-Open Patent Publication No. 20792/94 discloses a method for blood analysis by causing to leukocytes sufficient damage to allow the passage of a label through them. This method analyzes leukocytes by equally damaging normal leukocytes and immature leukocytes. However, immature leukocytes and normal leukocytes are not necessarily clearly separated according to this method. Furthermore, immature leukocytes treated by this method are permeable to a dye used as the label, and a method which does not cause damage to immature leukocytes is not disclosed in the publication.

SUMMARY OF THE INVENTION

An object of the present invention is to provide a method which can be used to measure immature leukocytes very precisely, and simultaneously perform classification of normal leukocytes and counting of leukocytes.

This invention provides a method for classifying and counting immature leukocytes, comprising the steps of:

(1) treating a hematological sample with a hemolytic agent which maintains immature leukocytes in a viable state and damages other leukocytes;

(2) staining the damaged leukocytes with a fluorescent dye which can stain damaged cells; and (3) measuring at least one kind of scattered light and at least one kind of fluorescence of the blood cells treated in the preceding step to classify and count leukocytes based on the intensities of the scattered light and the fluorescence.

The damaging of leukocytes in the invention refers to a procedure for permitting a dye, which usually does not pass through the cell membrane of a viable leukocyte, to permeate the cell membrane. According to the invention, normal leukocytes are damaged to allow permeation by the dye, while immature leukocytes are brought into an undamaged state, i.e., a state without permeability to the dye.

Normal white blood cells have a substance excluding function by which they exclude substances (e.g., dyes) unnecessary for the intracellular environment.

When a hemolytic agent of a specified composition is made to act on cells, some of the cell membrane lipid constituents of specified cells (e.g. normal leukocytes) are extracted (pulled out), to form in the cell membrane pores of a bore enough for the passage of a specified substance, although the mechanism of action in this case is not clear. As a result, dye molecules enter the specified cells and can thus stain the cells. Immature leukocytes, on the other hand, are not perforated with pores of a size sufficient for permeation by a dye (this state is called a viable state in the present invention), and thus are not stained with the dye. The immature leukocytes in the invention refer to immature cells which usually exist in the bone marrow and not in the peripheral blood, for example, blast cells, promyelocytes, myelocytes, and metamyelocytes. Promyelocytes, myelocytes and metamyelocytes may collectively be called immature granulo-cytes. Hematopoietic precursors of white blood cells, such as myelocytic stem cells (CFU-GEMN), neutrophil/macrophage colony forming cells (CFU-GM), and eosinophil colony forming cells (CFU-EOS), i.e., cells in the differentiation stage prior to blast cells, are also included in the range of the immature leukocytes of the invention. A state in which immature leukocytes are not stained, but other leukocytes are stained can be realized by mixing the hemolytic agent described below with the hematological sample. The hematological sample in the invention mainly refers to peripheral blood. Other preferred examples of the hematological sample are bone marrow fluid, samples containing blood components collected by apheresis or the like, and biological samples containing leukocyte constituents, such as abdominal cavity fluid and urine samples.

The hemolytic agents usable in the invention are aqueous solutions containing surface active agents. Preferred are those containing polyoxyethylene-based nonionic surface active agents of the structural formula indicated below. They are, preferably, hemolytic agents described in Japanese Laid-Open Patent Publication No. 273413/94. The hemolytic agents described in this publication contain (1) polyoxyethylene series nonionic surface active agents for fixing the cytoplasm and cell membrane of immature leukocytes, (2) solubilizers for damaging the cell membrane of blood cells and shrinking the cells, (3) amino acids for fixing the cytoplasm and cell membrane of immature leukocytes, and (4) buffers for making the pH of solutions 5.0 to 9.0 and their osmotic pressure 150 to 600 mOsm/kg and buffers for making the electrical conductivity of solutions 6.0 to 9.0 mS/cm. The present invention performs measurement optically, and is minimally affected by electrical conductivity. Thus, electrical conductivity is not restricted to the above range.

The above-mentioned polyoxyethylene-based nonionic surface active agents usable in the invention are expressed by the following structural formula

where $R_1$ denotes an alkyl, alkenyl or alkinyl group with 10 to 25 carbon atoms, $R_2$ denotes

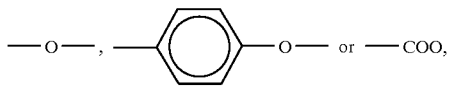

and n is 10 to 40.

Particularly preferred are polyoxyethylene (20) laurylether, polyoxyethylene (15) oleylether, and polyoxyethylene (16) oleylether.

The concentration of the polyoxyethylene-based nonionic surface active agent that can be used is 0.1 to 2.0 g/l (preferably 0.5 to 1.5 g/l) for polyoxyethylene (20) laurylether, 1 to 9 g/l (preferably 3 to 7 g/l) for polyoxyethylene (15) oleylether, or 5 to 50 g/l (preferably 15 to 35 g/l) for polyoxyethylene (16) oleylether, although the concentration differs depending on which surface active agent is used. The polyoxyethylene-based nonionic surface active agents have stronger cell damaging activity as the number of n decreases, and weaker cell damaging activity as the number of n increases, if these surface active agents have the same number of carbon atoms of the hydrophobic groups. If the surface active agents are the same in the number of n, the activity of damaging cells becomes higher as the number of carbon atoms of the hydrophobic groups decreases. In view of these facts and with reference to the above values, the required concentration of the surface active agent can be determined easily by experiment.

The solubilizer can be selected from among the following compounds:

(1) Sarcosine derivatives of the following formula or their salts

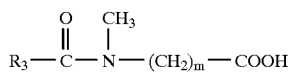

where $R_3$ is a $C_{10-22}$ alkyl group, and m denotes 1 to 5.

(2) Cholic acid derivatives of the following formula

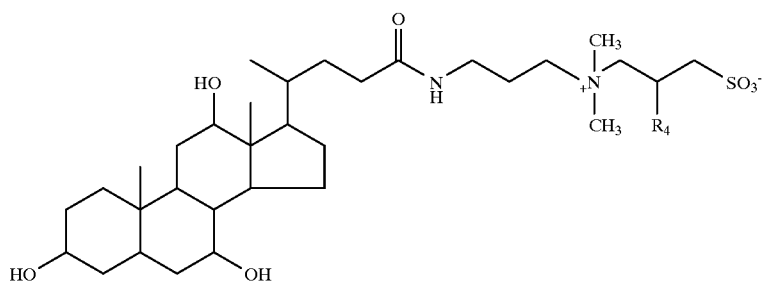

where R is a hydrogen atom or a hydroxyl group.

(3) Methylglucamide of the following formula

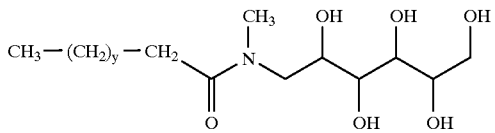

where y denotes 5 to 7.

The preferred concentration of the solubilizer is 0.2 to 2.0 g/l for the sarcosine derivative or its salt, 0.1 to 0.5 g/l for the cholic acid derivative, or 1.0 to 8.0 g/l for the methylglucamide. Preferred examples include N-lauroylsarcosine sodium salt, lauroylmethyl β-alanine sodium, lauroylsarcosine, CHAPS (3-[(3-cholamidopropyl)dimethylammonio]-1-propane-sulfonate), CHAPSO (3-[(3-cholamidopropyl)dimethylammonio]-2-hydroxy-1-propanesulfonate), MEGA8 (octanoyl-N-methylglucamide), MEGA9 (nonanoyl-N-methylglucamide), and MEGA10 (decanoyl-N-methylglucamide). Other compounds usable are n-octyl-glucoside, sucrose monocaprate, and N-formylmethyl-leucylalanine. The preferred concentration of any of these compounds is 0.01 to 50.0 g/l.

The amino acid may be one which constitutes protein. Preferred examples are glutamic acid, valine, and particularly preferred examples are sulfur-containing amino acids such as methionine, cystine and cysteine. Most preferable is methionine. The amount of the amino acid used is 1 to 50 g/l, and the preferred amount is 8 to 12 g/l for glutamic acid, while it is 16 to 24 g/l for methionine.

The buffer is Good's buffer such as HEPES or phosphate buffer. Preferably, a pH adjustor such as sodium hydroxide is added, and if desired, an osmotic pressure adjustor such as sodium chloride is further added, to make the pH 5.0 to 9.0 and the osmotic pressure 150 to 600 mOsm/kg.

The dyes used in the invention are dyes which can stain either damaged cells or immature leukocytes, and preferably can stain damaged cells. The dyes for staining damaged cells refer to dyes with a low ability to permeate viable cells. Generally, viable cells are distinguished from the outside of the cells by the cell membrane. The cell membrane is substance-selective so as not to allow the cellular passage of a substance which the cell does not need. An example of a dye with a low cell membrane permeating ability is Trypan Blue. Such dyes are generally acid dyes having acidic functional groups, such as carboxyl groups or sulfate groups. These dyes can stain cells having the cell membrane damaged, without staining viable cells. However, acid dyes tend to stain blood components other than leukocytes, such as platelets, and thus are not preferred for use in the invention. To attain the object of the invention, it is preferred to use such a dye as will stain a constituent present specifically in leukocytes. Particularly preferred are dyes having specificity for the cell nucleus, especially, for DNA, or dyes specific for RNA. For this purpose, some cationic dyes are preferred.

Generally, cationic dyes permeate the cell membrane of viable cells, staining the intracellular constituents. Particular cationic dyes (e.g., ethidium bromide and propidium iodide) are well known not to pass through viable cells, but to stain only damaged cells. The dyes usable for the purpose of the invention are not restricted. However, their examples include ethidium bromide and propidium iodide mentioned above, as well as ethidium-acridine heterodimer, ethidium diazide, ethidium homodimer-1, ethidium homodimer-2, ethidium monoazide, TOTO-1, TO-PRO-1, TOTO-3 and TO-PRO-3 sold by MOLECULAR PROBES (Handbook of Fluorescent Probes and Research Chemicals 5th Edition 1992–1994: MOLECULAR PROBES, INC., 1992). In addition, there are dyes preferred when He—Ne laser or red semiconductor laser is used as a light source. As these dyes, dyes of the following structural formula (I) have been found usable:

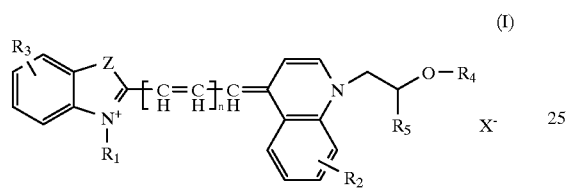

where $R_1$ is a hydrogen atom or a lower alkyl group, $R_2$ and $R_3$ each represents a hydrogen atom, a lower alkyl group or a lower alkoxy group, $R_4$ represents a hydrogen atom, an acyl group or a lower alkyl group, $R_5$ represents a hydrogen atom or an optionally substituted lower alkyl group, Z represents a sulfur atom, an oxygen atom or a lower alkyl-substituted carbon atom, n denotes 1 or 2, and $X^-$ represents an anion.

In the formula (I), the lower alkyl group for $R_1$ refers to a straight-chain or branched alkyl group having 1 to 6 carbon atoms. Its examples are methyl, ethyl, propyl, butyl, isobutyl, sec-butyl, ter-butyl, pentyl and hexyl. Of these, methyl and ethyl are preferred.

The lower alkyl group for $R_2$ and $R_3$ is the same as described above. The lower alkoxy group for them refers to an alkoxy group having 1 to 6 carbon atoms, whose examples are methoxy, ethoxy and propoxy. Of them, methoxy and ethoxy are preferred. More preferably, $R_2$ and $R_3$ are hydrogen atoms.

The acyl group for $R_4$ is preferably an acyl group derived from an aliphatic carboxylic acid. Examples are acetyl and propionyl, of which an acetyl group is preferred. The lower alkyl group for $R_4$ is the same as described above.

The lower alkyl group for $R_5$ is the same as described above. The optionally substituted lower alkyl group refers to a lower alkyl group which may be substituted by 1 to 3 hydroxyl groups or halogen atoms (fluorine, chlorine, bromine or iodine). Of them, methyl or ethyl substituted by one hydroxyl group is preferred.

The lower alkyl group for Z is the same as described above, and a sulfur atom is preferred for Z.

Examples of the anion for $X^-$ include a halogen ion (fluorine, chlorine, bromine or iodine ion), a boron halide ion ($BF_4^-$, $BC_{14}^-$ or $BBr_4^-$), a phosphorus compound ion, a perhalogenate ion, a fluorosulfate ion, a methylsulfate ion, and a tetraphenylboron compound ion having a halogen or a halogenated alkyl group as a substituent at the aromatic ring. Of them, a bromide ion or $BF_4^-$ is preferred.

Preferred examples of the dye of the formula (I) are the following dye A, dye B and dye C. A detailed method for synthesizing these dyes A, B and C is described in Japanese Laid-Open Patent Publication No. 104683/97.

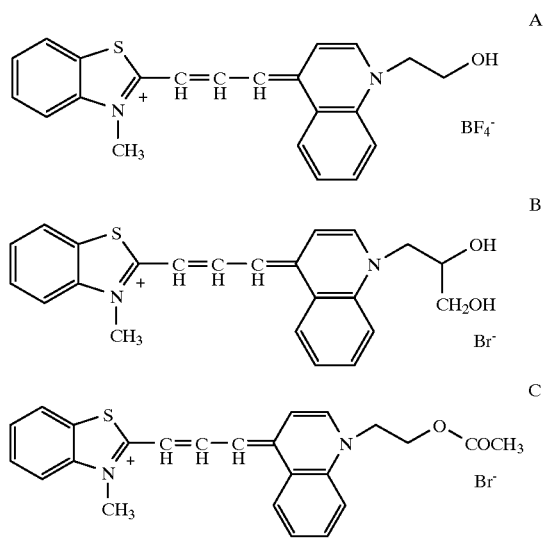

An example of the synthesis method is as follows:

The compound of the formula (I) with n=1 can be obtained, for example, by reacting a compound of the formula (II)

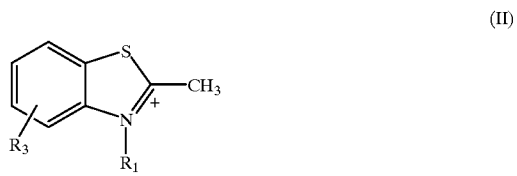

with N,N-disubstituted-formamidine, reacting the resulting product with a quinoline derivative of the formula (III)

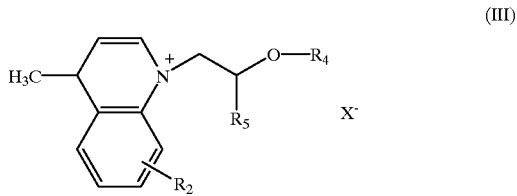

and then treating the resulting product with sodium borofluoride.

The compound of the formula (I) with N=2 can be obtained by using, say, malonaldehyde bis(phenylimine) salt instead of the N,N-disubstituted-formamidine in the above reaction.

The aforementioned handbook of MOLECULAR PROBES, INC. also discloses several dyes. The above-mentioned dyes are merely for exemplification, and in no way limit the present invention.

In preparing a sample for measurement, it suffices to mix a solution containing the aforementioned hemolytic agent and dye with a blood sample. Alternatively, it is advisable to dissolve the dye in a water-soluble organic solvent such as ethylene glycol, and mix the solution with the hemolytic agent just prior to use. By so doing, the storage stability of the dye can be enhanced. A suitable concentration can be determined depending on the dye used, and can be found experimentally with ease by those skilled in the art. Ethidium bromide, for instance, can be used in a concentration of 0.01 to 100 ppm, preferably, 0.1 to 30 ppm.

The mixing ratio of the blood sample to the hemolytic agent solution containing the dye is 1:10 to 1:1,000. The reaction temperature is 20 to 40° C., and the reaction time is 5 seconds to 5 minutes. Under these conditions, the reaction can be performed reliably. When the reaction temperature is high, it is desirable for the reaction time to be shortened.

To measure the prepared sample, a flow cytometer of a structure as shown in FIG. 1 can be used. A commercially available flow cytometer (e.g., FACScan, Becton Dickinson) can be used without need for modification. A light source can be selected suitably in harmony with the excitation wavelength of a fluorochrome to be used.

Scattered light to be detected may be forward scattered light (low-angled or high-angled) or side scattered light.

The present invention performs treatment with a hemolytic agent, staining with a dye capable of staining damaged cells, and measurement of scattered light and fluorescence in combination. By so doing, the invention enables the simultaneous classification and counting of normal leukocytes and immature leukocytes that was impossible with a conventional method, and also permits leukocyte counting in a single system.

DETAILED DESCRIPTION OF THE PREFERRED EMBODIMENTS

Figure 1:
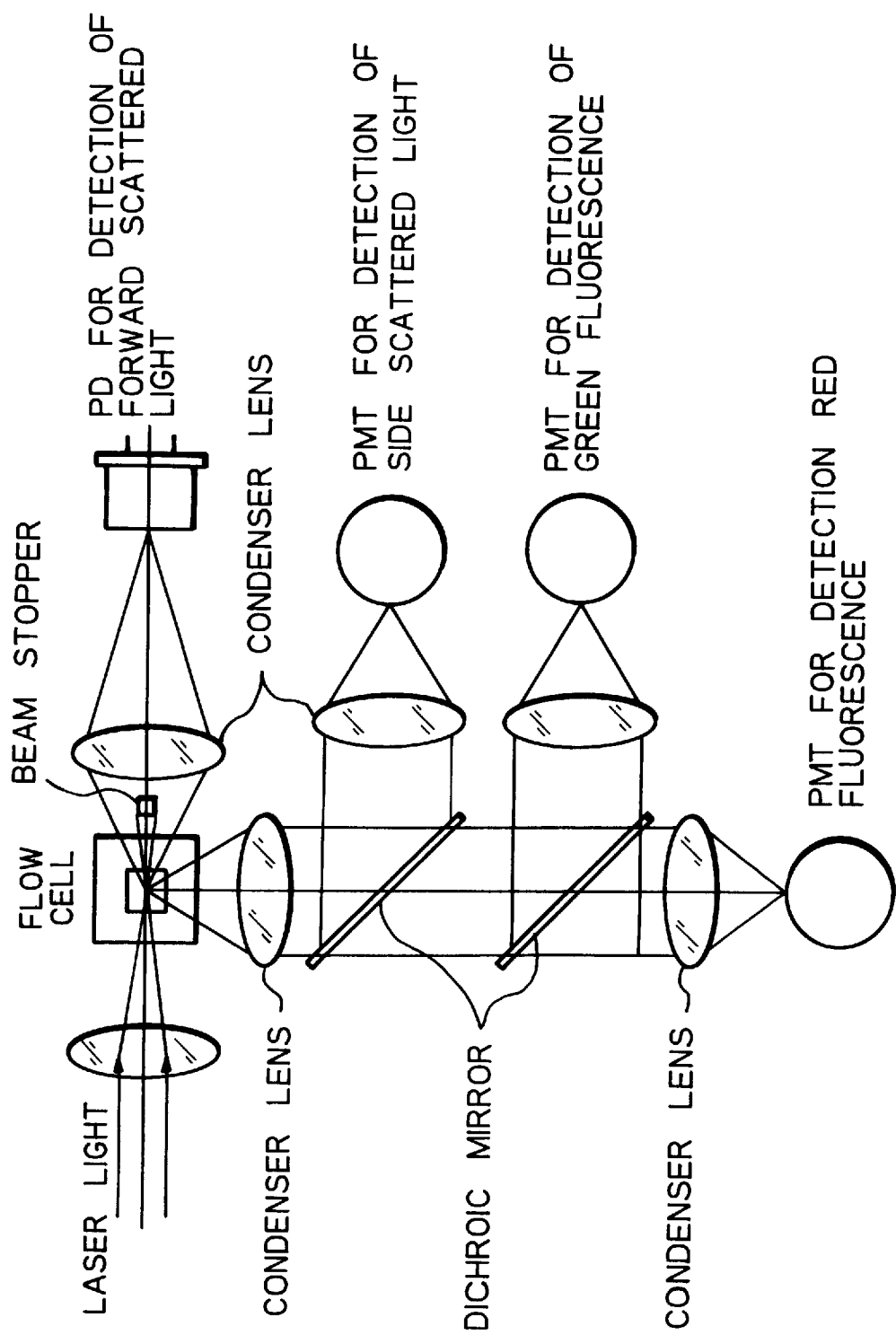
FIG. 1 is a schematic view of a flow cytometer usable in the method of the present invention.

The present invention will now be described by, but not restricted to, the following Examples.

EXAMPLE 1

Reagent for measurement:

| | |
|---|---|
| Polyoxyethylene (16) oleylether | 24.0 g/l |
| N-lauroylsarcosine sodium salt | 1.5 g/l |
| DL-methionine | 20.0 g/l |
| HEPES | 12.0 g/l |
| 1 N-NaOH | 0.3 g/l |
| NaCl | 4.0 g/l |
| Dye A | 3.0 mg/l |

1 ml of the above reagent was mixed with 33 µl of blood. Ten seconds later, the side scattered light and the red fluorescence were measured with a flow cytometer (light source: red semiconductor laser, wavelength: 633 nm).

The results obtained are shown in FIG. 2 (A to C). A represents the results of measurement on normal blood, B those on blood in which immature granulocytes appeared, and C those on samples in which immature granulocytes and blast cells appeared. In the drawings, Lymph signifies lymphocytes, Mono monocytes, Gran granulocytes, IG immature granulocytes, and Blast blast cells.

Figure 2A:
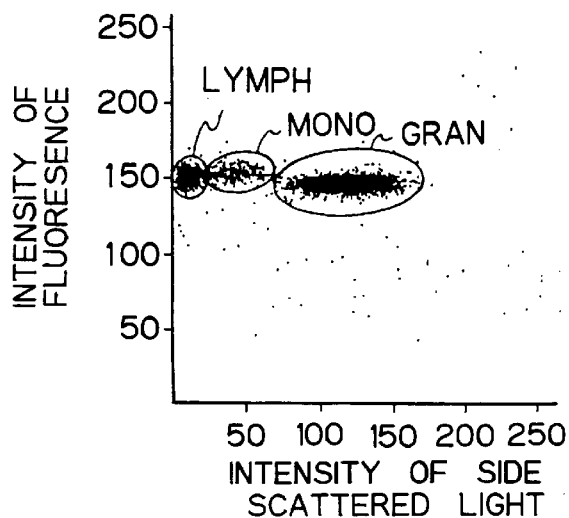
FIG. 2 shows the results of measurement using the method of the invention, with A representing those for normal blood, B those for blood in which immature granulocytes appeared, and C those for samples in which immature granulocytes and blast cells appeared.
Figure 2B:
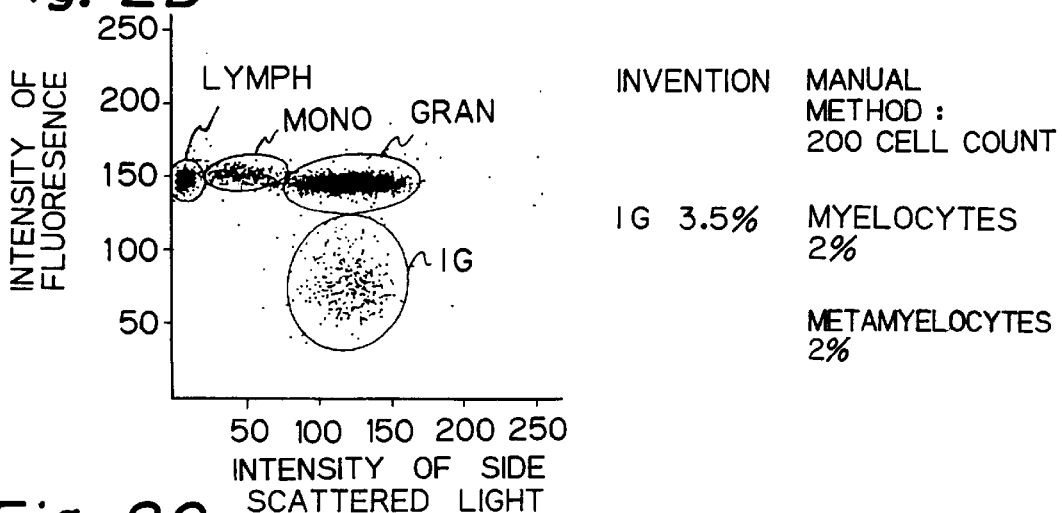
Figure 2C:
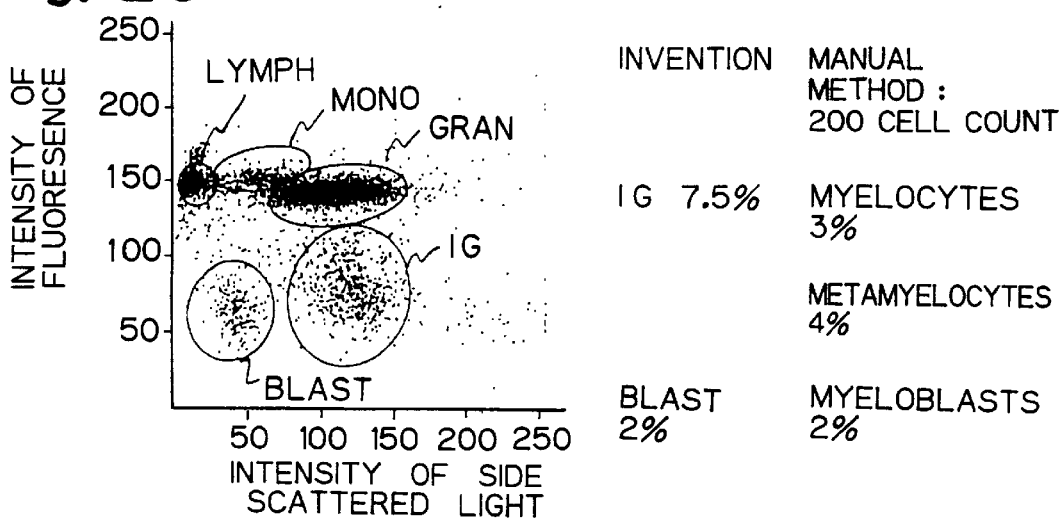
Figure 3C:
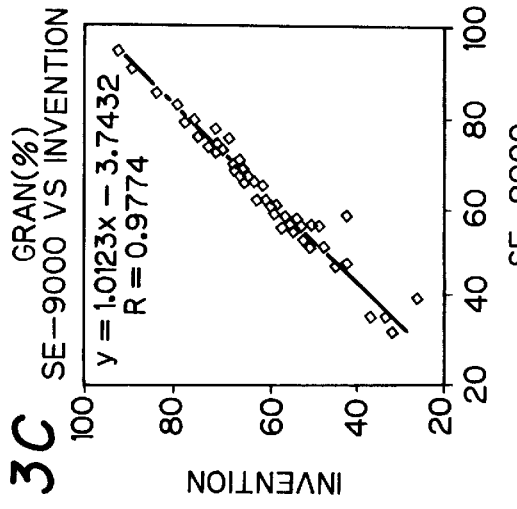
FIG. 3 shows the results of correlation analysis based on comparisons between the results of measurement by the method of the invention and the results of measurement by a conventional method with A representing lymphocytes, B representing monocytes, C representing granulocytes and D representing the total count of leukocytes (WBC)
Figure 3D:
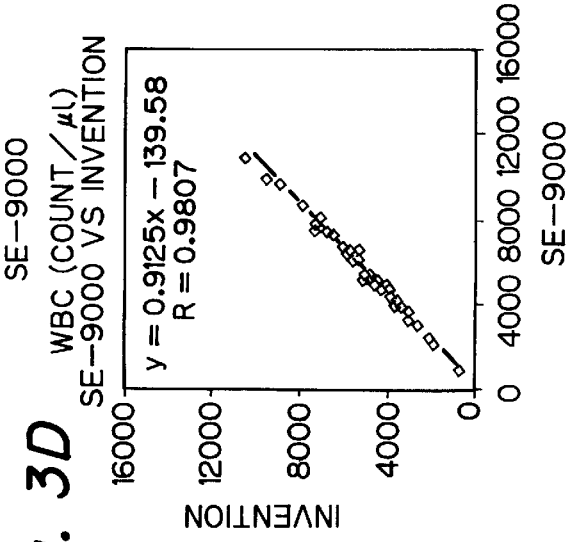
Figure 3A:
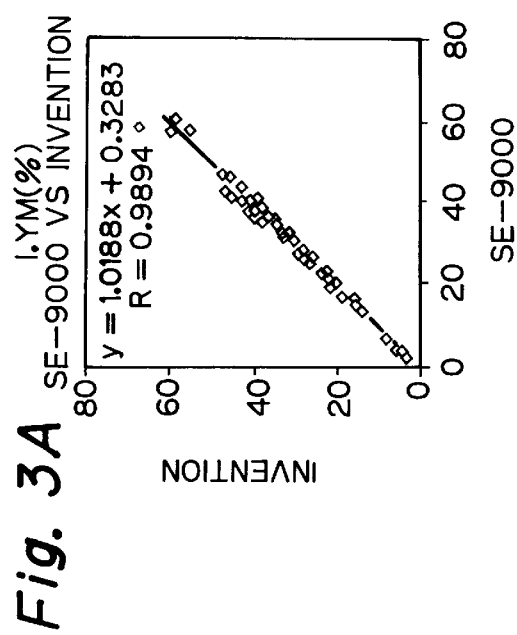
Figure 3B:
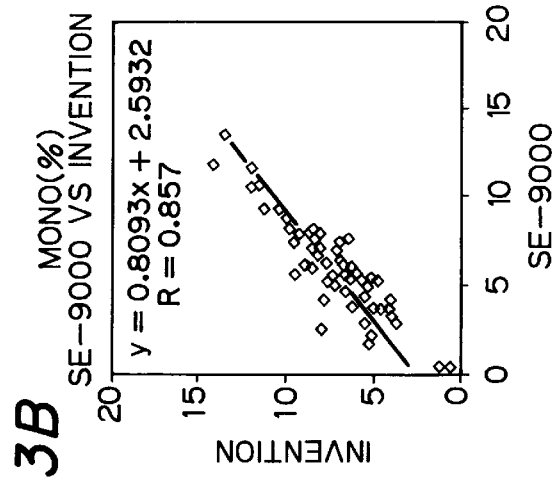

In FIG. 2A, leukocytes are classified into three categories, lymphocytes, monocytes and granulocytes. In FIG. 2B, leukocytes are further classified into immature granulocytes in addition to the normal three classes. In FIG. 2C, leukocytes are further classified into immature granulocytes and blast cells in addition to the normal three classes.

Then, the results of measurement by the measuring method of the invention were compared with the results of measurement by a conventional method to make correlation analysis. The conventional method was performed using a multi-parameter blood cell autoanalyzer (SE-9000, TOA MEDICAL ELECTRONICS).

The results obtained are shown in FIG. 3(A to D). In terms of the proportions of lymphocytes (A), monocytes (B) and granulocytes (C), as well as the total count of leukocytes (WBC, indicated in D of FIG. 3), a good correlation was obtained between the results by the conventional method and the results by the method of the invention. The proportion of granulocytes determined by SE-9000 was the total proportion of NEUT (neutrophils)+EO (eosinophils)+BA (basophils).

EXAMPLE 2

Figure 4:
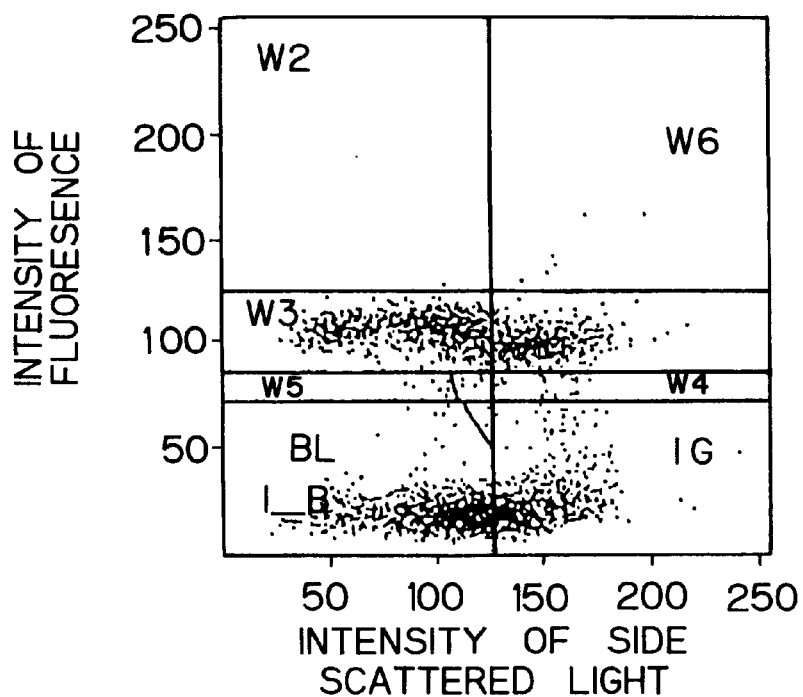
FIG. 4 shows the results of measurement by the method of the invention made in samples in which hematopoietic precursor cells appeared after administration of G-CSF.

Using the same reagent as used in Example 1, samples in which hematopoietic precursor cells appeared after G-CSF treatment were measured for side scattered light and red fluorescence by means of a flow cytometer. The results are shown in FIG. 4. A cell population was observed in a region with a low fluorescence intensity, a region for immature leukocytes.

Hematopoietic precursor cells were separated by utilizing their CD34 positiveness, and measurements were made. First, monocyte-rich samples were prepared by a blood component analyzer. Then, the samples were reacted with magnetic beads (Dynabeads™; commercially available as DYNAL) bound to anti-CD34 monoclonal antibodies (Becton Dickinson Immunocytometry System Co., Ltd.). A magnetic cell separator (Isolex™, Baxter Co., Ltd.) was used to separate hematopoietic precursor cells positive for CD34. The separated cells were treated with an enzyme (chymopapain) to separate the CD34-positive cells from the magnetic beads.

Figure 5:
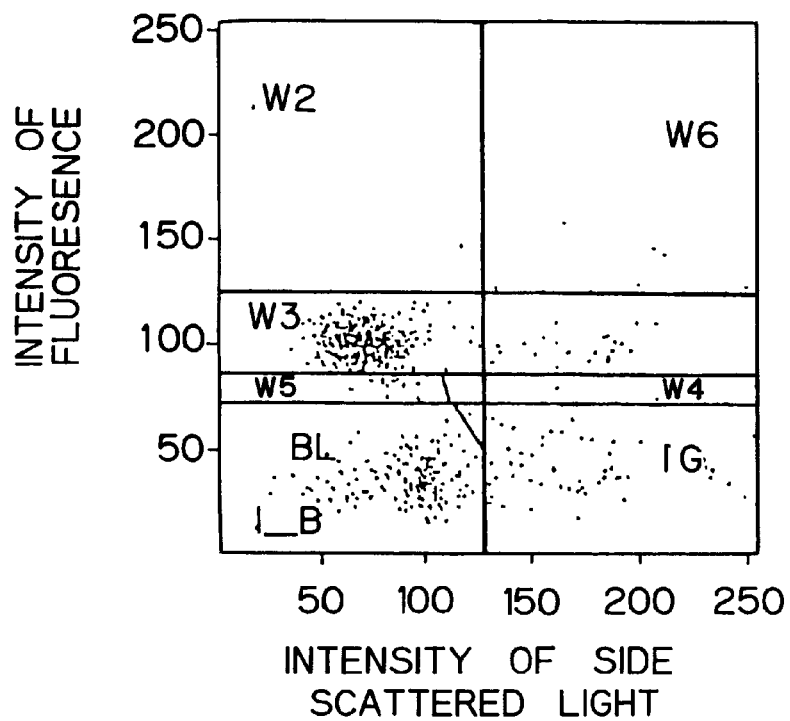
FIG. 5 shows the results of measurement by the method of the invention made in CD34-positive hematopoietic precursor cells after separation.

The so prepared samples were measured for lateral scattered light and red fluorescence by means of a flow cytometer using the same reagent. The results are shown in FIG. 5. Similarly, a cell population was observed in a region with a low fluorescence intensity, a region for immature leukocytes.

What is claimed is:

1. A method for classifying and counting immature leukocytes, and simultaneously detecting normal leukocytes to determine a total leukocyte count comprising the steps of:

(1) treating a hematological sample containing blood cells with a hemolytic agent which maintains immature leukocytes in a viable state and damages other leukocytes:

(2) staining the damaged leukocytes with a fluorescent dye which can stain damaged cells; and (3) measuring at least one kind of scattered light and at least one kind of fluorescence of the blood cells in said hematological sample treated in the preceding steps (1) and (2) to classify and count immature leukocytes and to simultaneously detect normal leukocytes based on intensities of scattered light and fluorescence, and thereby determining the total leukocyte count.

2. The method of claim 1, wherein the normal leukocytes are further classified into at least three categories and counted.

3. The method of any one of claims 1 and 2, wherein the hemolytic agent contains the following components:
   (1) a polyoxyethylene series nonionic surface active agent for fixing the cytoplasm and cell membrane of immature leukocytes,
   (2) a solubilizer for damaging the cell membrane of blood cells other than immature leukocytes and shrinking the cells,
   (3) an amino acid for fixing the cytoplasm and cell membrane of immature leukocytes, and
   (4) a buffer for making the pH of the hemolytic agent 5.0 to 9.0 and the osmotic pressure of the hemolytic agent 150 to 600 m)sm/kg.

4. The method of any one of claims 1 and 2, wherein the fluorescent dye is selected from the group consisting of:
   (1) compounds of the formula (I)

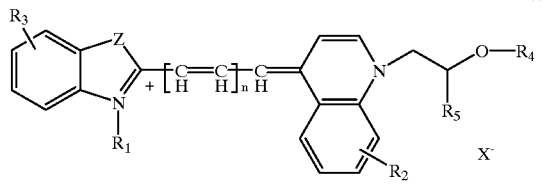

where $R_1$ is a hydrogen atom or a lower alkyl group, $R_2$ and $R_3$ each represent a hydrogen atom, a lower alkyl group or a lower alkoxy group, $R_4$ represents a hydrogen atom, an acyl group or a lower alkyl group, $R_5$ represents a hydrogen atom or an optionally substituted lower alkyl group, Z represents a sulfur atom, an oxygen atom or a lower alkyl-substituted carbon atom, n denotes 1 or 2, and $X^-$ represents an anion,
   (2) ethidium bromide and propidium iodide; and
   (3) ethidium-acridine heterodimer, ethidium diazide, ethidium homodimer-1, ethidium homodimer-2, ethidium monoazide, TOTO-1, TO-PRO-1, TOTO-3 and TO-PRO-3.

5. The method of claim 3, wherein the fluorescent dye is selected from the group consisting of:
   (1) compounds of the formula (I)

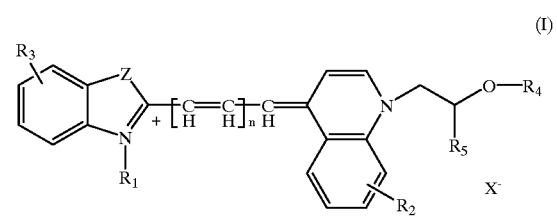

where $R_1$ is a hydrogen atom or a lower alkyl group, $R_2$ and $R_3$ each represent a hydrogen atom, a lower alkyl group or a lower alkoxy group, $R_4$ represents a hydrogen atom, an acyl group or a lower alkyl group, $R_5$ represents a hydrogen atom or an optionally substituted lower alkyl group, Z represents a sulfur atom, an oxygen atom or a lower alkyl-substituted carbon atom, n denotes 1 or 2, and $X^-$ represents an anion,
   (2) ethidium bromide and propidium iodide; and
   (3) ethidium-acridine heterodimer, ethidium diazide, ethidium homodimer-1, ethidium homodimer-2, ethidium monoazide, TOTO-1, TO-PRO-1, TOTO-3 and TO-PRO-3.

* * * * *